United States Patent [19]

Thorwart et al.

[11] Patent Number: 5,137,897
[45] Date of Patent: Aug. 11, 1992

[54] 2-SUBSTITUTED 4-(3-ALKYL-5-TERT.-BUTYL-4-HYDROXYPHENYL) THIAZOLES, PROCESSES FOR THEIR PREPARATION, PHARMACEUTICALS CONTAINING THEM AND THEIR USE

[75] Inventors: Werner Thorwart, Hochheim am Main; Rudolf Schleyerbach, Hofheim am Taunus; Robert Bartlett, Darmstadt; Klaus U. Weithmann, Hofheim am Taunus, all of Fed. Rep. of Germany

[73] Assignee: Hoechst Aktiengesllschaft, Frankfurt am Main, Fed. Rep. of Germany

[21] Appl. No.: 626,784

[22] Filed: Dec. 13, 1990

[30] Foreign Application Priority Data

Dec. 15, 1989 [DE] Fed. Rep. of Germany ....... 3941438

[51] Int. Cl.$^5$ ................. C07D 277/28; C07D 277/30; A61K 31/425
[52] U.S. Cl. .................................. 514/365; 548/204; 548/205
[58] Field of Search ...................... 548/203, 204, 205; 514/365

[56] References Cited

U.S. PATENT DOCUMENTS

4,535,165  8/1985  Moore ................................ 548/204
4,636,516  1/1987  Kubo ................................. 514/365

FOREIGN PATENT DOCUMENTS

0276805  8/1988  European Pat. Off. .
1695252  6/1966  Fed. Rep. of Germany .
62-132871  6/1987  Japan .

OTHER PUBLICATIONS

Houben-Weyl, Meth. der. org. Chem., vol. IX, pp. 762–768 (1966).
Prof. Dr. W. Walter et al., Angew. Chem., vol. 78, No. 10, 1966, pp. 517–521 and 531–532.
Houben Weyl, vol. V/4, 1960, pp. 171–189.
L. C. King et al., J. of Org. Chem. vol. 29, 1964, pp. 3459–3461.
K. Inami et al., Bull. Chem. Soc. Jap., vol. 58, 1985, pp. 355–360.
R. J. Smith et al., Biochemical Pharmacology, vol. 37, No. 9, 1988, pp. 1667–1672.
K. U. Weithmann et al., Arzneim.-Forsch./Drug. Res., vol. 35(I), No. 6, 1985, pp. 947–952.

Primary Examiner—Robert Gerstl
Attorney, Agent, or Firm—Finnegan, Henderson, Farabow, Garrett and Dunner

[57] ABSTRACT

Novel substituted thiazoles of the formula I

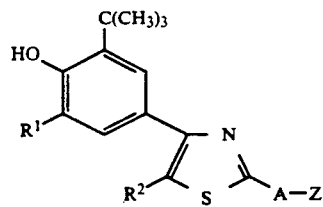

in which $R^1$ is a saturated or unsaturated, straight-chain or branched $C_1$-$C_5$-alkyl group,
$R^2$ is a hydrogen atom or an alkyl radical having 1 to 3 carbon atoms,
A is an intermediate chain of the formula $-(CH_2)_n-Y-CR^3R^4-$; $-CH=CR^3-(CH_2)_m-$
or $-CH=N-O-(CH_2)_n-$ where
Y is a single bond, an oxygen or sulfur atom or a carbonyl group,
$R^3$ and $R^4$ are identical or different and are a hydrogen atom or an alkyl radical having up to two carbon atoms, m is a number from 0 to 3 and n is a number from 1 to 4, and
Z is a tetrazole or CN group, or a radical of the formula

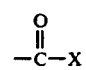

X is a hydroxyl group or a radical of the formula $R^5O-$ or $R^6R^7N-$, where $R^5$ is a straight-chain or branched $C_1$-$C_4$-alkyl radical which is optionally substituted by hydroxyl, $C_1$-$C_3$-alkoxy or $C_1$-$C_3$-alkylamino,
$R^5$ and $R^7$ are identical or different and are a hydrogen atom, a straight-chain or branched $C_1$-$C_6$-alkyl radicall or, for the case in which $R^6$ is a hydrogen atom or a $C_1$-$C_4$-alkyl radical,
$R^7$ is a hydroxyl, a $C_1$-$C_3$-alkoxy or a tetrazol-5-yl group or X, together with the structural element $-A-(C=O)-$, is a radical of the formula II

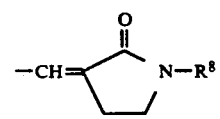

where $R^8$ is a hydrogen atom, a $C_1$-$C_3$-alkyl radical or a $C_1$-$C_3$-alkoxy radical, and physiologically tolerable salts of such compounds of the formula I in which X is a hydroxyl or hydroxyamino group, are prepared by various processes.

They are preferably suitable for the treatment and prophylaxis of inflammatory diseases - in particular inflammatory rheumatic diseases.

8 Claims, No Drawings

2-SUBSTITUTED 4-(3-ALKYL-5-TERT.-BUTYL-4-HYDROXYPHENYL) THIAZOLES, PROCESSES FOR THEIR PREPARATION, PHARMACEUTICALS CONTAINING THEM AND THEIR USE

DESCRIPTION

The present invention relates to novel 2-substituted 4-(3-alkyl-5-tert.-butyl-4-hydroxyphenyl)thiazoles, to processes for their preparation and to their use as active compounds in medicaments for the treatment of inflammatory diseases, in particular inflammatory rheumatic disorders.

It is known that a general disadvantage of all classical non-steroidal antiinflammatories is that they indeed permit the elimination or relief of the symptoms pain, inflammation and swelling, but leave any pathological processes, which additionally cause the progressive course of the inflammatory rheumatic diseases, uninfluenced to the greatest possible extent. There is therefore an urgent need for therapeutically utilizable antirheumatics which, by virtue of their profile of action, can be expected to have a far-reaching and lasting intervention in the inflammatory process. Promising starting points for these are offered by those pharmaceuticals which, in addition to inhibition of cyclooxygenase, intervene to an increased extent in the alternative pathway of arachidonic acid metabolism (by inhibiting, for example, 5-lipoxygenase and thus suppressing the excessive formation of the pro-inflammatory leukotrienes) and which may also have antioxidative properties and therefore deactivate the highly reactive oxygen free radicals which, as inflammatory mediators, cause progressive cell and tissue destruction in the rheumatic joints.

Pharmaceuticals with this trend of indication are described, for example, in EP-A-0,276,805; they are products based on substituted 3-phenyl-7H-thiazolo[3,2b][1,2,4]triazin-7-ones of the following formula

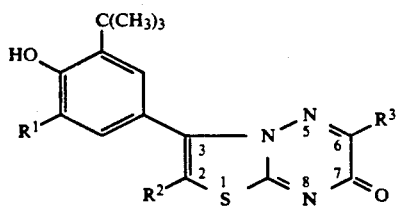

in which
R$^1$ is a straight-chain or branched alkyl group having 1 to 4 carbon atoms, hydroxymethyl or an aminomethyl group of the formula

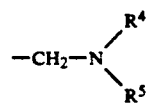

R$^2$ is a hydrogen atom or an alkyl radical having 1 to 3 carbon atoms and
R$^3$ is a hydrogen atom, a straight-chain or branched alkyl group having 1 to 4 carbon atoms, hydroxymethyl or the abovementioned aminomethyl group, where
R$^4$ and R$^5$ are identical or different and are a hydrogen atom or a straight-chain or branched alkyl radical having 1 to 4 carbon atoms, or both radicals, together with the nitrogen atom to which they are bonded, form a 5- to 7-membered saturated ring having 4 to 6 carbon atoms or having 4 or 5 carbon atoms and additionally a further heteroatom in the form of O, S or NR$^6$, and R$^6$ has the meaning of hydrogen or (C$_1$-C$_4$)alkyl.

Furthermore, thiazole derivatives substituted in a specific manner are known which, in addition to an antiatherosclerotic action, should have inflammation- and fever-alleviating as well as pain-relieving properties (DE-A-1695,252); however, the pharmacological effects are not explained in more detail there. For these thiazole derivatives, two substituents are characteristic, namely
a phenyl or alkyl radical, which can in turn be substituted in the phenyl or aryl moiety by halogen, NO$_2$ or CF$_3$, and
a radical of the formula -CH$_2$-COOH in this form or a form derived therefrom.

The thiazole derivatives - substituted by the 3,5-di-tert.-butyl-4-hyiroxyphenyl radical - of the following formula should also have antiinflammatory and pain-relieving (analgesic) properties (JP-A-87,132,871):

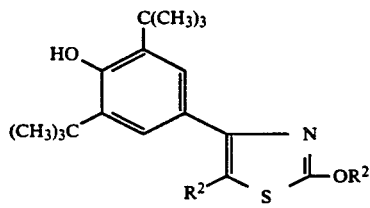

in which
R$^1$=H, hydroxy(lower)alkyl, hydroxyimino(lower)alkyl, lower alkoxyimino(lower)alkyl, —CHO, —COOH, —CN, —NO$_2$, halogen, —NCS or alkyleneamino and
R$^2$=H, lower alkyl, lower acyl, lower alkoxycarbonyl
with the proviso that in the case of R$^1$=H, R$^2$ must be lower acyl or lower alkoxycarbonyl.

The 3,5-di-tert.-butyl hydroxyphenyl thiazole derivatives of the following formula:

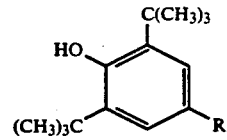

in which
R=thiazolyl, halothiazolyl or methylthiazolyl
described, inter alia, in US-A-4,535,165 are also of similar structure.

The compounds should have antiinflammatory activity.

In the desire to satisfy, if possible better than previously, the need described at the beginning for therapeutically utilizable antirheumatics which, by virtue of their profile of action, can be expected to have a far-reaching and lasting intervention in the inflammatory process, it has now been found that this aim is achieved by the provision of novel thiazole derivatives for which, specifically, a 3-alkyl-5-tert.-butyl-4-hydroxyphenyl substituent and a further substituent containing a carboxyl group or a group derived therefrom, is characteristic As a result of the combination of these two substituents in the thiazole ring, the immunopathological processes - underlying the chronic inflammatory phase are inhibited to an increased extent and an advantageous antirheumatic mechanism of action is thus achieved By virtue of their cyclooxygenase and lipoxygenase-inhibiting properties, their capability to deactivate oxygen free radicals by means of their antioxidative potential and their property of intervening advantageously in the disturbed immune system, the novel thiazole derivatives are suitable for use in pharmaceuticals, in particular in those which are indicated in inflammatory rheumatic diseases.

The invention thus relates to substituted thiazoles of the formula I

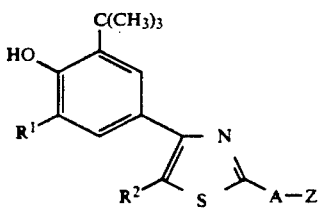

in which
R$^1$ is a saturated or unsaturated, straight-chain or branched C$_1$-C$_5$-alkyl group,
R$_2$ is a hydrogen atom or an alkyl radical having 1 to 3 carbon atoms,
A is an intermediate chain of the formula —(CH$_2$)$_n$—Y—CR$^3$R$^4$—;
—CH=CR$^3$—(CH$_2$)$_m$—or
—CH=N—O—(CH$_2$)$_n$— where
Y is a single bond, an oxygen or sulfur atom or a carbonyl group,
R$^3$ and R$^4$ are identical or different and are a hydrogen atom or an alkyl radical having up to two carbon atoms, and
m is a number from 0–3 and
n is a number from 1 to 4, and
Z is a tetrazole or CN group, or a radical of the formula

X is a hydroxyl group or a radical of the formula R$^5$O- or R$^6$R$^7$N-, where R$^5$ is a straight-chain or branched C$_1$-C$_4$-alkyl radical which is optionally substituted by hydroxyl, C$_1$-C$_3$-alkoxy or C$_1$-C$_3$-alkylamino, R$^6$ and R$^7$ are identical or different and are a hydrogen atom, a straight-chain or branched C$_1$-C$_6$-alkyl radical or, for the case in which R$^6$ is a hydrogen atom or a C$_1$-C$_4$-alkyl radical,
R$^7$ is a hydroxyl, a C$_1$-C$_3$-alkoxy or a tetrazol-5-yl group or X, together with the structural element —A—(C=O)—, is a radical of the formula II

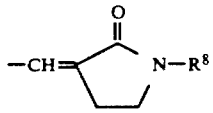

where R$^8$ is a hydrogen atom, a C$_1$-C$_3$-alkyl radical or a C$_1$-C$_3$-alkoxy radical, and physiologically tolerable salts of such compounds of the formula I in which X is a hydroxyl or hydroxyamino group.

Preferred compounds of the formula I in this case are those in which
R$^1$ is a tert.-butyl or methyl group,
R$^2$ is hydrogen or methyl,
A is an intermediate chain of the formula —(CH$_2$)$_n$—Y—CR$^3$R$^4$— where
Y is a single bond or an oxygen atom, R$^3$ and R$^4$ are identical or different and are a hydrogen atom or a methyl radical, and n is a number of 1 or 2, and
X is a hydroxyl group or a radical of the formula R$^5$O-or R$^6$R$^7$N-, where R$^5$ is a straight-chain or branched C$_2$-C$_3$-alkyl radical, R$^6$ is a hydrogen atom or a methyl radical and R$^7$ is a hydroxyl, methoxy or tetrazol-5-yl group.

Among these, compounds of the formula I are in turn particularly preferred in which
R$^1$ is a tert.-butyl group
R$^2$ is hydrogen or methyl,
A is an intermediate chain of the formula —(CH$_2$)$_n$—Y—CR$^3$R$^4$— where
Y is a single bond, R$^3$ and R$^4$ are a hydrogen atom and n is a number of 1 or 2 and
X is a hydroxyl group or an R$^6$R$^7$N radical, where R$^6$ is a hydrogen atom or a methyl radical and R$^7$ is a hydroxyl or methoxy group.

A very particularly preferred compound is 3-[4-(3,5-di-tert.-butyl-4-hydroxyphenyl)thiazol-2-yl-]propionic acid, i.e. the compound of the formula I where
R$^1$=tert.-butyl,
R$^2$=H,
A=—(CH$_2$)$_n$—Y—CR$^3$R$^4$—, in which R$^3$=R$^4$=H, Y =a single bond and n =1.

The invention furthermore relates to processes for the preparation of the compounds of the formula I according to the invention. Compounds of the formula I in which A is an intermediate chain of the formula —(CH$_2$)$_n$—Y—CR$^3$R$^4$—, where Y, R$_3$, R$^4$ and n have the abovementioned meaning and X is an R$^5$O radical, can be obtained by procedure a).

Process a) comprises reacting a thiacarboxamide of the formula III

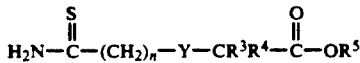

with 2-halo-1-phenylalkanones of the formula IV

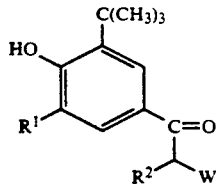

(IV)

in which R¹ and R² have the abovementioned meaning and W is a halogen, preferably chlorine or bromine, to give the compounds of the formula Ia according to the invention

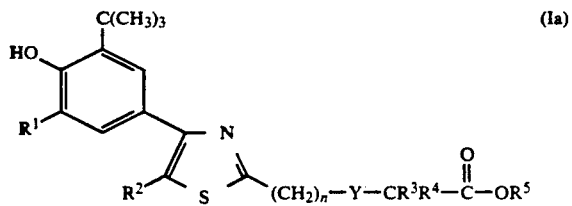

(Ia)

having the meanings mentioned above for R¹, R², R³, R⁴, R⁵, Y and n.

Suitable solvents for the reaction, in which equimolar amounts of the reaction components are usually employed, are in particular polar solvents, i.e., for example, alcohols, such as methanol, ethanol, the various propanols or butanols, but also lower aliphatic carboxylic acids, such as formic acid and acetic acid, and also ethyl acetate, acetone, butan-2-one, dimethylformamide or acetonitrile or mixtures of said solvents.

The reaction is in general carried out at temperatures between about 20° C. and the boiling point of the reaction medium used, particularly between about 50° C. and 80° C., the reaction times being between less than one hour and about 3 hours The thiacarboxamides of the formula III required for process a) can be prepared by processes known to the person skilled in the art, for example by addition of hydrogen sulfide to the corresponding nitriles in the presence of a base (see Houben-Weyl, Methoden der organischen Chemie (Methods of Organic Chemistry), Volume IX, pp.762-768). Preferred bases, which can be used in catalytic to equimolar amounts, are amines such as, for example, triethylamine or pyridine, but also alcoholates and alkali metal hydrogen sulfides. The reaction is carried out in an organic solvent, in particular an alcohol such as methanol, ethanol or propanols, or in pyridine; a mixture of pyridine and triethylamine is particularly suitable. The reaction temperature is between about 0° C. and the boiling point of the solvent used, the reaction is preferably carried out at room temperature (about 20°-30° C). A further embodiment of the process is the use of 0,0-dialkyl dithiophosphates, in particular the methyl or ethyl ester, as a source of hydrogen sulfide (S. W. Walter and K. D. Bode, Angew. Chem. 1966, 78, pp. 517-532), in which the hydrogen chloride for the cleavage of the primary addition product is introduced into the reaction mixture at temperatures from about −10° C. to 20° C., preferably about −10° C. to 0° C.

The 2-halo-1-phenylalkanones of the formula IV also used as starting materials are known from the literature or can easily be prepared from the 1-(3-alkyl-5-tert.-butyl-4-hydroxyphenyl)alkanones by reaction with a suitable halogenating agent by the methods described in HoubenWeyl Vol. V/4 pp.171-189 (1960).

A suitable compound IV is, for example, 2-bromo-1-(3,5-di-tert.-butyl-4-hydroxyphenyl)ethanone or 2-bromo-1-(3-methyl-5-tert.-butyl-4-hydroxyphenyl)ethanone, which can be prepared by halogenation of the appropriately substituted 1-phenylalkanones with elemental bromine or with copper(II) bromide according to a process by L. C. King and G. K. Ostrum, J. Org. Chem. 1964, 29, pp. 3459-3461.

Sulfuryl chloride, in particular, is suitable for obtaining those compounds of the formula IV in which Z is a chlorine atom, and is preferably reacted with the appropriate 1-phenylalkanones at temperatures between about 10° C. and 30° C. in the presence of inert solvents such as, for example, methylene chloride or chloroform. A further preparation process is the Friedel-Crafts acylation of 2- alkyl-6-tert.-butylphenols, preferably with chloroacetyl chloride, in the presence of Lewis acids, such as, for example, aluminum chloride or boron trifluoride.

Compounds of the formula I in which $A=-CH=CR^3(CH_2)_m-$ and X is preferably an $R^5O$ radical can be prepared by process b). Process b) comprises reacting a thiazole aldehyde of the formula V

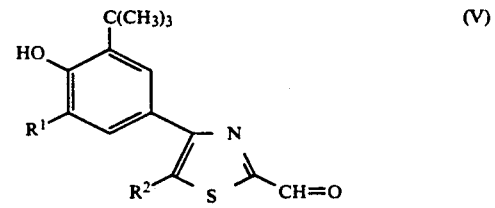

(V)

in an olefination reaction with a dialkyl phosphonate of the formula VI

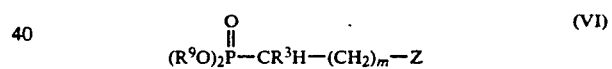

(VI)

in which $R^9$ is a $C_1-C_3$-alkyl radical, to give the alkenoic acid esters of the formula I b according to the invention

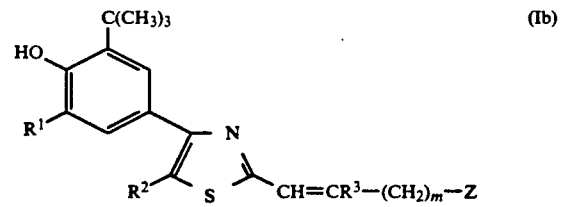

(Ib)

in which R¹, R², Z, R³ and R⁵ have the abovementioned meaning.

The thiazole aldehydes of the formula V necessary as intermediates for this are advantageously prepared according to procedure a) by reaction of a 2-halo-1phenylalkanone of the formula IV with dialkoxythioacetamides, such as, for example, diethoxythioacetamide (cf. K. Inami and T. Shiba, Bull. Chem. Soc. Jap. 1985, 58, pp. 352-360). To liberate the aldehyde, the corresponding acetal is warmed with dilute mineral acids such as hydrochloric acid o sulfuric acid.

A preferred process for the preparation of the compound I b is its reaction in a PO-activated olefination with dialkyl phosphates of the formula VI in which $R^3$ is a hydrogen atom or methyl and $R^5$ and $R^9$ are an ethyl radical, under the standard conditions known to the person skilled in the art. In a preferred embodiment, dimethylformamide is used as the solvent and sodium hydride as the base, the reaction in general being carried out at the boiling point of the solvent.

Compounds of the formula I in which the structural element —A— together with —C(=O)X is a pyrrolidinone radical of the formula II, can be prepared by procedure c). Process c) comprises reacting a thiazole aldehyde of the formula V in an olefination reaction with a 3-halo-pyrrolidinone of the formula VII

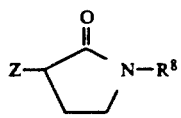

(VII)

together with a phosphinic or phosphoric acid ester in the presence of a strong base to give the compounds I c according to the invention

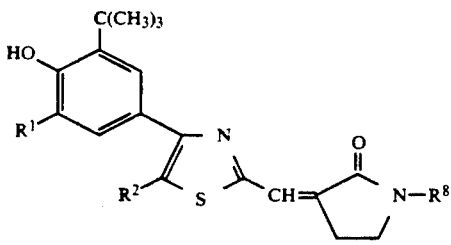

(Ic)

having the meanings indicated above for $R^1$, $R^2$, $R^8$ and Z.

The preferred embodiment of process c) is the reaction of a 3-halopyrrolidinone of the formula VII, in particular of that one in which Z is a bromine atom, with a phosphine such as triphenylphosphine to give the corresponding quaternary phosphonium salts, where in the case of $R^8$ = hydrogen, compound VII is previously treated with an acetylating agent such as acetic anhydride to protect the free amide nitrogen. These intermediates can in general be reacted with the aldehydes of the formula V without further working up by the standard processes customary for a Wittig reaction. In this case, warming of the reaction components in an inert solvent, in particular an alcohol such as ethanol or dimethylformamide in the presence of a base such as triethylamine, a sodium or potassium alcoholate, sodium hydride or potassium hydride or sodium hydroxide or potassium hydroxide, has proved particularly advantageous. The reaction is carried out at temperatures from about 20° C. up to the boiling point of the solvent used, preferably in a range of from about 60°-80° C.

Compounds of the formula I in which A comprises an oxime of the formula —CH=N—O—(CH$_2$)$_n$— as an intermediate chain can be prepared by process d). Process d) comprises condensing a compound of the formula V with a hydroxylamine of the formula VIII

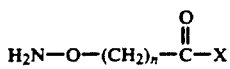

(VIII)

in which X and n have the abovementioned meaning, to give the compounds I d according to the invention

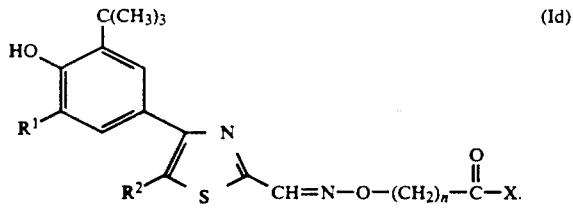

(Id)

The reaction is advantageously carried out using equimolar amounts of the reaction components in aqueousalcoholic solution; but it is also carried out in other inert solvents such as pyridine, dimethylformamide and alcohols such as methanol, ethanol and the various propanols and butanols and also in mixtures of these solvents. The hydroxylamine derivatives of the formula VIII are in this case expediently employed in the form of their acid addition salts, such as the hydrochlorides, hydrobromides or sulfates. In this case, it is recommended to add an acid-binding agent, for example alkali metal hydroxides or carbonates or, alternatively, an organic base, such as triethylamine, in at least stoichiometric amount. The reaction is carried out at temperatures between about 20° C. and the boiling point of the solvent, preferably between 40° C. and 70° C.

Compounds of the formula I in which, in the intermediate chain A, Y is an oxygen atom, $R^3$ and $R^4$ are a $C_1$-$C_2$-alkyl radical, n=1 and X is a hydroxyl group, can also be prepared by process e). Process e) comprises reacting a hydroxymethylthiazole of the formula IX

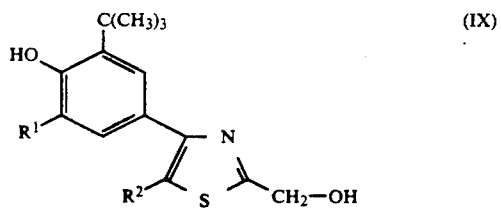

(IX)

with a ketone of the formula $R^3$—CO—$R^4$, where $R^1$, $R^2$ and $R^4$ have the abovementioned meaning, in the presence of a tri- or tetrahalogenated alkane and a strong base, to give the compounds of the formula I e according to the invention

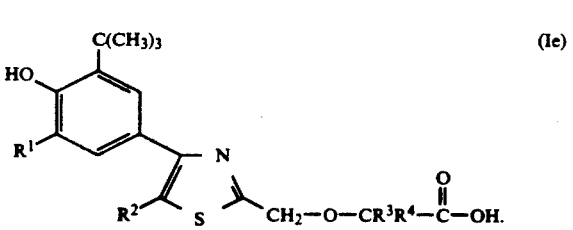

(Ie)

The hydroxymethylthiazoles of the formula IX necessary for this can be prepared by reduction of the appropriate aldehydes of the formula V by methods which are known in principle. Suitable reductants are complex hydrides such as sodium borohydride or lithium borohydride or lithium aluminum hydride. The reaction is preferably carried out in an inert organic solvent, such as tetrahydrofuran, an ether such as, for example, diethyl ether or tert.-butyl methyl ether, toluene or methylene chloride in a preferred temperature range of from about 20° C. to 80° C.

A further process for the preparation of the precursors of the formula IX according to process variant a) is the reaction of a 2-halo-1-phenylalkanone of the formula IV with benzoyloxythioacetamide (J. F. Olin and T. B. Johnson, Recl. Trav. Chim. Pays-Bas 1931, 50, 72) and subsequent hydrolysis of the benzoyl protecting group in the presence of a base such as sodium or potassium hydroxide or sodium or potassium alcoholate in alcohols, such as methanol or ethanol, as the preferred solvent.

To prepare the compounds of the formula I e, alcohols of the formula IX are reacted with tri- or tetra-substituted alkanes, such as bromoform, iodoform, carbon tetrachloride and, in particular, chloroform and with a ketone such as, for example, acetone, butan-2-one or pentanones, using a strong base. The strong base can be, for example, an alkali metal hydroxide, such as sodium or potassium hydroxide, preferably in solid form.

A preferred embodiment of this process is the reaction of compounds of the formula IX with chloroform and acetone in the presence of powdered sodium hydroxide and at the boiling point of the reaction components.

Compounds of the formula I in which X is a hydroxyl group can also be prepared by process f), which comprises hydrolyzing a compound of the formula I, preferably I a, I b, or I c, in which X is $OR^5$.

The hydrolysis is carried out by known standard processes in the presence of a base, such as sodium, potassium, barium or calcium hydroxide, or potassium alcoholate. Solvents used are the lower alcohols, such as methanol, ethanol or the various propanols or their mixtures with water.

Compounds of the formula I in which X is an $R^5O$ or $R^6R^7N$ group having the meaning mentioned above for $R^5$, $R^6$ and $R^7$ can be prepared by process g), which comprises condensing a compound of the formula I in which X is a hydroxyl group with the appropriate alcohol $R^5OH$, amine or hydroxylamine $HNR^6R^7$ by processes which are known in principle to the person skilled in the art.

For these processes, suitable condensing agents are those which are proven in peptide chemistry, such as, for example, carbonyldiimidazole, dicyclohexylcarbodiimide, diethoxyphosphonyl chloride, diethoxyphosphonyl azide, phosphorus oxychloride, propylphosphonic anhydride and diphenylphosphonyl chloride. The condensation is advantageously carried out in a solvent. Depending on the condensing agent used, nearly all common organic solvents, such as hydrocarbons (saturated or aromatic), chlorinated hydrocarbons, ethers, lower ketones such as acetone or butanone, tert. amides such as dimethylformamide, dimethylacetamide or N-methylpyrrolidone, lower alcohols such as methanol, ethanol, isopropanol, n-, iso- or tert.-butanol and even aqueous systems or mixtures (homogeneous or two-phase) of said organic solvents with water are suitable.

An embodiment of this process is the reaction of the compounds of the formula I in which X is a hydroxyl group with dicyclohexylcarbodiimide in a solvent, particularly halogenated hydrocarbons such as methylene chloride or chloroform, followed by the addition of a basic catalyst such as 4-diethylamino- or pyrrolidinopyridine and of the alcohol $R^5OH$ or the amine HNRR, at temperatures of about 20°-40° C. Alternatively, the carboxylic acids of the formula I where X =OH can first be converted into an activated derivative, such as an acid chloride or mixed anhydride, and this can then be reacted with an amine or hydroxylamine $HNR^6R^7$, preferably in the presence of an auxiliary base such as sodium hydrogencarbonate, sodium or potassium carbonate, sodium or potassium hydroxide or a tert. amine such as pyridine or triethylamine. A large number of methods for the activation of carboxylic acids are familiar to the person skilled in the art, for example reaction with thionyl chloride, phosphorus trichloride, silicon tetrachloride, phosgene or oxalyl chloride to give the acid chloride or reaction with chloroformic acid esters or sulfonyl chlorides (methanesulfonyl chloride, trifluoromethanesulfonyl chloride, benzenesulfonyl chloride) in the presence of bases, preferably of tert. amines such as triethylamine or pyridine, to give the mixed anhydrides.

A preferred variant of this embodiment of process g) is the reaction of a compound of the formula I in which $R^1$, $R^2$ and A have the abovementioned meaning and X is a hydroxyl group, with $HNR^6 R^7$ in the presence of silicon tetrachloride in pyridine at temperatures of about −20° C. to 40° C., preferably at room temperature.

Compounds of the formula I in which $R^1$, $R^2$ and A have abovementioned meaning and X is an $R^6R^7N$ group can also be prepared by process h), which comprises reacting a compound of the formula I, in which X is an $R^5O$ radical, with the appropriate base $HNR^6R^7$.

The reaction is preferably carried out in a suitable organic solvent such as an alcohol (methanol, ethanol, n-propanol, n-butanol, isopropanol, 2-ethoxyethanol, 2-methoxyethanol), an ether (preferably tetrahydrofuran, dioxane, 1,2-dimethoxyethane or diethylene glycol dimethyl ether) or a hydrocarbon, such as xylene, toluene, mesitylene, tetralin or decalin. An excess of the amine or hydroxylamine can also be used as the solvent. The reaction is carried out at temperatures in the range from about 20° C. up to the boiling point of the solvent used, and temperatures of about 40° C. to 120° C., particularly of about 40° to 80° C., are preferred.

Compounds of the formula I a in which $R^1$, $R^2$ and $R^5$ have the abovementioned meaning, $R^3$ is a hydrogen atom or methyl, $R^4$ is a hydrogen atom and Y is a single bond, can also be prepared by process i). Process i) comprises reacting a compound of the formula I b according to the invention with suitable reductants. A preferred embodiment is the catalytic hydrogenation of the olefins on palladium or platinum on carbon as the catalyst in a polar solvent such as alcohols (methanol, ethanol) or acetic acid, at pressures of about 1 to 3 atm and temperatures between about 20° C. and 60° C., preferably at room temperature.

The compounds of the formula I according to the invention, if they contain a carboxyl group, can form salts with inorganic or organic bases. The present invention therefore also relates to these salts. Preferred salts are those with inorganic bases, particularly the physiologically acceptable alkali metal salts, in particular sodium or potassium salts.

The 2-substituted 4-(3-alkyl-5-tert.-butyl-4-hydroxyphenyl)thiazoles of the formula I according to the invention and their corresponding salts are particularly suitable by virtue of their useful pharmacological properties for use as active compounds in pharmaceuticals, in particular in those for the treatment of inflammatory rheumatic diseases. They can either be administered by themselves, for example in the form of microcapsules, in mixtures with one another or in combination with suitable auxiliaries and/or excipients.

The invention thus also relates to pharmaceuticals which are composed of at least one compound of the formula I and/or at least one of its appropriate salts or contain at least one of these active compounds in addition to pharmaceutically suitable and physiologically tolerable excipients, diluents and/or other auxiliaries.

The pharmaceuticals according to the invention can be administered orally, systemically, rectally or, if desired, also parenterally, oral administration being preferred.

Suitable solid or liquid pharmaceutical preparation forms are, for example, granules, powders, coated tablets, tablets, (micro)capsules, suppositories, syrups, elixirs, suspensions, emulsions, drops or injectable solutions and preparations with sustained release of active compound, in whose preparation customary auxiliaries, such as excipients, disintegrants, binders, coating agents, swelling agents, glidants or lubricants, flavorings, sweeteners or solubilizers are used. Frequently used auxiliaries are, for example, magnesium carbonate, titanium dioxide, lactose, mannitol and other sugars, talc, lactoprotein, gelatin, starch, cellulose and its derivatives, animal and vegetable oils, polyethylene glycols and solvents, such as, for example, sterile water and mono- or polyhydric alcohols, for example glycerol.

The pharmaceutical preparations are preferably produced and administered in dosage units, each unit containing a specific dose of at least one compound according to formula I and/or at least one appropriate salt as the active constituent. In the case of solid dosage units, such as tablets, capsules, coated tablets, or suppositories, this dose can be up to about 800 mg, but preferably about 100 to 500 mg.

For the treatment of an adult patient suffering from inflammatory rheumatic diseases—depending on the activity of the compounds according to formula I and/or the corresponding salts in humans—daily doses of about 100 to 2000 mg of active compound, preferably about 300 to 1100 mg, are indicated for oral administration. Under certain circumstances, however, higher or lower daily doses may also be appropriate. The daily dose can be administered both by administration once in the form of an individual dosage unit or else several smaller dosage units and also by repeated administration of subdivided doses at specific intervals.

Finally, the compounds of the formula I and the corresponding salts can also be formulated together with other suitable active compounds, for example antiuricopathics, thrombocyte aggregation inhibitors, analgesics and other steroidal or non-steroidal antiinflammatories, for the production of the abovementioned pharmaceutical preparations.

The structure of all compounds described below was checked by elemental analysis and IR and $^1$H-NMR spectra. The compounds of the formula I prepared according to the following examples and analogously are summarized in Table 1.

EXAMPLE 1

Ethyl 3-[4-(3,5-di-tert.-butyl-4-hydroxyphenyl)thiazol-2-yl]propionate according to process a)

a$_1$) 2-Bromo-1-(3,5-di-tert.-butyl-4-hydroxyphenyl)ethanone 20.6 g (83 mmol) of 1-(3,5-di-tert.-butyl-4-hydroxyphenyl)ethanone were dissolved in 50 ml of methylene chloride with stirring and heated to boiling, and 14.4 g (90 mmol) of bromine were added dropwise in the course of 15 minutes. The mixture was then heated under reflux for a further 2 hours and cooled, 50 ml of water were added, and the organic phase was separated and dried over sodium sulfate. After removing the solvent under reduced pressure, the solid residue was recrystallized from methylcyclohexane.

Yield: 20.5 g (72 % of theory)
Melting point: 105°–108° C.
$C_{16}H_{23}BrO_2$ (MW = 327.3)

a$_2$) 3-(Ethoxycarbonyl)thiopropionamide

Hydrogen sulfide was introduced with stirring at room temperature into a solution of 31.8 g (0.25 mol) of ethyl 3-cyanopropionate and 34.6 ml (0.25 mol) of triethylamine in 75 ml of pyridine for 9 hours. After allowing to stand overnight, the reaction mixture is rendered acidic with 2N hydrochloric acid with cooling and extracted several times with ethyl acetate. The combined organic phase, which is dried over sodium sulfate, is carefully concentrated under reduced pressure. The oily residue remaining (35.0 g = 87 % of theory) is composed of about 87 % of 3-(ethoxycarbonyl)thiopropionamide and 13 % of ethyl 3-cyanopropionate according to GC analysis.

a$_3$) Ethyl 3-[4-(3,5-di-tert.-butyl-4-hydroxyphenyl)thiazol-2-yl]propionate 36.0 g (0.11 mol) of 2-bromo-1-(3,5-di-tert.-butyl-4-hydroxyphenyl)ethanone from step a$_1$) and 17.7 g (0.11 mol) of 3-(ethoxycarbonyl)thiopropionamide (reactive component of the substance mixture obtained from step a$_2$) were heated under reflux in 100 ml of ethyl acetate for 1.5 hours. After cooling and treating with an NaHCO$_3$ solution, the organic phase was separated, dried and concentrated under reduced pressure. Thoroughly stirring the remaining oily residue with petroleum ether (40°–60° C.) gave a crystalline precipitate.

Yield: 33.4 g (78 % of theory).
Melting point: 55°–56° C.,
$C_{22}H_{31}NO_3S$ (MW = 389.6),
Analysis ed: C 67.83 %, H 8.02 %, N 3.60 %, S 8.23 %,
Found: C 67.81 % H 8.05 % N 3.57 % S 8.44 %.

The compound was also prepared by process i) by catalytic hydrogenation of ethyl 3-[4-(3,5-di-tert.-butyl-4-hydroxyphenyl) thiazol-2-yl]acrylate as follows:

A solution of 6 g (15.5 mmol) of ethyl 3-[4-(3,5-di-tert.-butyl-4-hydroxyphenyl)thiazol-2-yl]acrylate (for whose preparation see Example 2) was hydrogenated in the presence of 2 g of palladium/carbon (10 %) in 200 ml of glacial acetic acid in a Parr apparatus until hydrogen was no longer absorbed. Filtering off the catalyst and concentrating the mixture under reduced pressure gave a residue which, as in the case of a$_3$), first taken up in ethyl acetate, treated with NaHCO: solution and finally after evaporating the solvent led to an oily residue. The product was obtained as colorless crystals from this after treatment with petroleum ether.

Yield: 4.3 g (71 % of theory),
Melting point: 56°–57° C., $C_{22}H_{31}NO_3S$ (MW = 389.6),
Analytical and spectroscopic data confirm the identity of the product obtained with the compound prepared according to procedure a).

EXAMPLE 2

Ethyl 3-[4-(3,5-di-tert.-butyl-4-hydroxyphenyl)thiazol-2-yl]acrylate according to process b)

b$_1$) 4-(3,5-di-tert.-butyl-4-hydroxyphenyl)-2-formylthiazole 90 g (0.27 mol) of 2-bromo-1-(3,5-di-tert.-butyl-4-hydroxyphenyl)ethanone from step a$_1$) and 42.4 g (0.26 mol) of diethoxythioacetamide were stirred at room temperature in 200 ml of ethanol for 30 minutes. After removing the solvent under reduced pressure, the residue was treated in the presence of heat with 200 ml of ethyl acetate. The crystalline precipitate of the corresponding diethyl acetal produced in this way was dissolved in 1500 ml of acetone to liberate the aldehyde group, 230 ml of 4 N hydrochloric acid were added and the mixture was stirred at room temperature for 2 hours. After neutralization with Na$_2$CO$_3$ solution, a precipitate deposit which, after filtering off, was recrystallized again from petroleum ether.

Yield: 63.4 g (77 % of theory),
Melting point: 99°-100° C.;
C$_{18}$H$_{23}$NO$_2$S (MW=317.5),
Analysis: Calculated: C 68.10 %, H 7.30 %, N 4.41 %, S 10.10 %;
Found: C 67.86 %, H 7.29 %, 4.35 %, S 9.97 %, b$_2$) Ethyl 3-[4-(3,5-di-tert.-butyl-4-hydroxyphenyl)thia-zol-2-yl]acrylate 6.6 g (0.22 mol) of 80 % pure sodium hydride were introduced in portions with stirring into a solution of 31.7 g (0.1 mol) of the aldehyde from step b ) and 23.3 g (0.1 mol) of triethyl phosphonoacetate in 400 ml of dry dimethylformamide, the reaction temperature being kept below 30° C. by water-cooling. After stirring at room temperature for 3 hours, the mixture is extracted several times with ethyl acetate after adding 375 ml of 4 N sulfuric acid. The combined ester phases are twice extracted by shaking with 300 ml of saturated NaHCO$_3$ solution in each case, washed with water, dried over sodium sulfate and concentrated in vacuo. Recrystallization of the residue from methanol gave yellow crystals.

Yield: 33.3 g (86 % of theory),
Melting point: 126°-127° C. C$_{22}$H$_{29}$NO$_3$S (MW=387.5).
Analysis: Calculated: C 68.18 %, H 7.54 %, N 3.61 %, S 8.27 %;
Found: C 67.87 %, H 7.66 %, N 3.59 %, S 8.31 %

EXAMPLE 3

3-[4-(3,5-Di-tert.-butyl-4-hydroxyphenyl)thiazol-2-yl]propionic acid according to procedure f)

After addition of 6 ml of 10 N sodium hydroxide solution to a solution of 7.5 g (19 mmol) of the ester from Example 1 in 35 ml of ethanol, the mixture was stirred at room temperature for 30 minutes. It was then adjusted to pH 1 using 4 N hydrochloric acid. The crystals obtained in this were filtered off with suction, and partitioned between ethyl acetate and water. The organic phase separated off was concentrated in vacuo after drying and the residue was recrystallized from petroleum ether/ diisopropyl ether (10 : 1).

Yield: 5.9 g (86 % of theory)
Melting point: 154°-155° C.
C$_{20}$H$_{27}$NO$_3$S (MW=361.5), Analysis: Calculated: C 66.45 %, H 7.53 %, N 3.87 %, S 8.87 %,
Found: C 66.55 %,H 7.75 % N 3.86 %,S 8.68 %,

EXAMPLE 4

3-[4-(3,5-Di-tert.-butyl-4-hydroxyphenyl)thiazol-2-yl methylidene]pyrrolidin-2-one according to procedure c)

16.0 g (91 mmol) of 3-bromopyrrolidin-2-one were heated to boiling in 30 ml of acetic anhydride for 1 hour. After evaporating the reaction mixture t dryness under reduced pressure, the residue was dissolved in 50 ml of tetrahydrofuran and, after adding 26.2 g (0.1 mol) of triphenylphosphine, heated under reflux for 5 hours. It was then concentrated again, the residue was dissolved in 300 ml of ethanol and 24.7 g (78 mmol) of the aldehyde from Example 2 b$_1$) and 27 ml (0.36 mol) of triethylamine were added. After heating the mixture at 70° C. for 2 hours, the yellow precipitate was filtered off and washed with ethanol. The crystal magma is dissolved in about 2 l of chloroform, the solution is washed several times with saturated sodium chloride solution and dried over Na$_2$SO$_4$, and the chloroform phase is concentrated to a third. Yellow crystals deposit on allowing to stand for a relatively long time.

Yield: 24.7 g (81 % of theory),
Melting point: 244°-245° C.
C$_{22}$H$_{28}$N$_2$O$_2$S (MW=384.5)
Analysis: Calculated: C 68.72 %, H 7.34 %, N 7.28 %, S 8.34 %,
Found: C 68.45 %, H 7.13 %, N 6.89 %, S 7.97 %.

EXAMPLE 5

2-[4-(3,5-Di-tert.-butyl-4-hydroxyphenyl)thiazol-2-ylmethylidene)aminooxy]acetic acid according to procedure d)

A solution of 6.4 g (0.05 mol) of carboxymethoxyamine hydrochloride in 20 ml of water and 2 g (0.05 mol) of sodium hydroxide in 200 ml of water are simultaneously added dropwise with stirring to a solution of 15.9 g (0.05 mol) of the aldehyde from Example 2 b ) in 200 ml of methanol. After further stirring at 50° C. for 1.5 hours, the methanol is largely removed by distillation in vacuo and the residue is extracted several times with ethyl acetate. The combined extracts are washed with water, dried over Na$_2$SO$_4$ and evaporated in vacuo. The oily residue becomes crystalline after treating with petroleum ether (40°-60° C.).

Yield: 13.8 g (71 % of theory),
Melting point: 178°-180° C.; C$_{20}$H$_{26}$N$_2$O$_4$S (MW=390.5).
Analysis: Calculated: C 61.52 %, H 6.71 %, N 7.17 %, S 8.21 %,
Found: C 61.44 %, H 6.85 %, N 6.96 %, S 8.02 % .

EXAMPLE 6

2-[4-(3,-Di-tert -butyl-4-hydroxyphenyl)thiazol-2-yl)methoxy]-2-methylpropionic acid according to procedure d)

d$_1$) [4-(3,5-Di-tert.-butyl-4-hydroxyphenyl)-2-hydroxy-methylthiazole 117.8 g (0.36 mol) of 2-bromo-1-(3,5-di-tert.-butyl-4-hydroxyphenyl)ethanone and 72.1 g (0.34 mol) of benzoyloxythioacetamide are dissolved in 300 ml of ethanol and stirred at room temperature for 4 hours. The crystals forming during the course of this are filtered off and washed with a little ethanol. To liberate the hydroxyl group, 139.4 g of the isolated benzoyl ester (m.p.: 198-199° C. as the hydrobromide) were taken up in 600 ml of ethanol, 45.6 g (0.69 mol) of 85 % strength potassium hydroxide in 30 ml of water were added and the mixture was subsequently stirred at room temperature for half an hour. The mixture is then concentrated, water is added and it is extracted several times with ethyl acetate. After drying over $Na_2SO_4$, ethanolic hydrochloric acid is added to the combined extracts, the alcohol depositing in the form of the hydrochloride.

Yield: 78.6 g (65 % of theory),
Melting point: 185°-186° C. (as hydrochloride),
$C_{18}H_{26}ClNO_2S$ (MW=355.9).
Analysis:
Calculated: C 60.74 %, H 7.36 %, Cl 9.96 %, N 3.94 %, S 9.01 %,
Found: C 60.49 %, H7.56 %, Cl 10.05 %, N 6.96 %, S 9.05 %.

d₂) 2-[4-(3,5-Di-tert.-butyl-4-hydroxyphenyl)thiazol-2-yl)methoxy]-2-methylpropionic acid 9.6 g (0.031 mol) of the alcohol from step e₁7.56 %, Cl 10.05 %, N 6.96 %, S 9.05 %.) in the form of the free base are mixed with 6.0 g (0.15 mol) of powdered sodium hydroxide in 44 ml of acetone and the suspension is heated to reflux. 4.8 g (0.04 mol) of chloroform in 10 ml of acetone are then added dropwise and the mixture is heated at reflux temperature for a further 5 hours. The solvents are then evaporated in vacuo and the residue is partitioned between diisopropyl ether and water. The organic phase is separated off and the aqueous phase is acidified to pH 2 with concentrated hydrochloric acid after extracting again with ether and extracted several times with methylene chloride. The combined methylene chloride extracts are dried, filtered and concentrated. The residue is purified by column chromatography on silica gel (90-130) eluent: methylene chloride/methanol (50 1), and crystallized using a little petroleum ether (40°-60° C.).

Yield: 3.1 g (26 % of theory),
Melting point: 158°-159° C.; $C_{22}H_{31}NO_4S$ (MW=405.6).
Analysis: Calculated: C 65.16 %, H 7.70 %, N 3.45 %, S 7.91 %,
Found: C 65.03 %, H 7.89 %, N 3.37 %, S 7.81 %.

EXAMPLE 7

3-[4-(3.-butyl-4-hydroxyphenyl)thiazol-2-yl]propionylhydroxamic acid according to procedure g)

First 1.4 g of dimethylformamide, then 5.3 g (42 mmol) of oxalyl dichloride are added at 0° C. to a solution of 6.7 g (18.6 mmol) of the acid from Example 3) in 250 ml of methylene chloride and the mixture is subsequently stirred for 1 hour. During the dropwise addition of a solution of 7.7 g (111 mmol) of hydroxylamine hydrochloride in 65 ml of THF and 13 ml of water and 11.2 g (111 mmol) of triethylamine, the reaction temperature is allowed to rise to 30° C. and the mixture is subsequently stirred for a further 12 hours. 300 ml of 2N hydrochloric acid are then added and the organic phase is separated off. The aqueous phase is extracted again with methylene chloride and the combined organic phases are washed with satd. $NaHCO_3$ and NaCl solution, dried over $Na_2SO_4$ and concentrated in vacuo. The residue solidifies after adding petroleum ether (40°-60° C.).

Yield: 3,8 g (55 % of theory)
Melting point: 182°-183° C.
$C_{20}H_{28}N_2O_3S$ (MG=376,6),
Analysis 63,80 %, H 7,50 %, N 7,44 %, S 8,52 %;
Found: C 63,95 %, H 7,61 %, N 7,41 %, S 8,63 %.

TABLE 1

Compounds according to formula I (see claim 1)

| Example | $R^1$ | $R^2$ | A | X | Melting point °C. |
|---|---|---|---|---|---|
| 1 | $(H_3C)_3C-$ | H | $-(CH_2)_2-$ | $-OC_2H_5$ | 55-57 |
| 2 | $(H_3C)_3C-$ | H | $-CH=CH-$ | $-OC_2H_5$ | 126-127 |
| 3 | $(H_3C)_3C-$ | H | $-(CH_2)_2-$ | $-OH$ | 154-155 |
| 4 | $(H3C)3C-$ | H | 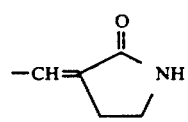 | | 244-245 |
| 5 | $(H_3C)_3C-$ | H | $-CH=N-O-CH_2-$ | $-OH$ | 178-180 |
| 6 | $(H_3C)_3C-$ | H | 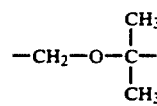 | $-OH$ | 158-159 |
| 7 | $(H_3C)_3C-$ | H | $-(CH_2)_2-$ | $-NH-OH$ | 182-183 |
| 8 | $(H_3C)_3C-$ | H | $-CH_2-$ | $-O-C_2H_5$ | 79-80 |
| 9 | $(H_3C)_3C-$ | H | $-CH_2-$ | $-OH$ | 88-89 (decomp.) |
| 10 | $(H_3C)_3C-$ | H | $-(CH_2)_3-$ | $-OH$ | 123-124 |
| 11 | $(H_3C)_3C-$ | H | $-CH=CH-$ | $-OH$ | 195-196 |
| 12 | $(H_3C)_3C-$ | H | $-CH=CH-$ | $-OCH_3$ | 129-130 |
| 13 | $(H_3C)_3C-$ | H | $-(CH_2)_2-$ | $-OCH_3$ | 77-78 |
| 14 | $(H_3C)_3C-$ | $CH_3$ | $-(CH_2)_2-$ | $-OC_2H_5$ | 67-68 |
| 15 | $(H_3C)_3C-$ | $CH_3$ | $-(CH_2)_2-$ | $-OH$ | 132-133 |
| 16 | $CH_3-$ | H | $-(CH_2)_2-$ | $-OC_2H_5$ | 127-129 |
| 17 | $CH_3-$ | H | $-(CH_2)_2-$ | $-OH$ | 138-140 |
| 18 | $(H_3C)_3C-$ | H | $-CH_2-S-CH_2-$ | $-OH$ | 146-148 |
| 19 | $(H_3C)_3C-$ | H | $-(CH_2)_2-$ | $-N(CH_3)OH$ | 79-80 |
| 20 | $(H_3C)_3C-$ | H | $-(CH_2)_2-$ | $-NHOCH_3$ | 160-161 |

TABLE 1-continued

| Example | R¹ | R² | A | X | Melting point °C. |
|---|---|---|---|---|---|
| 21 | $(H_3C)_3C-$ | H | $-(CH_2)_2-N\overset{H}{\underset{}{-}}$ | 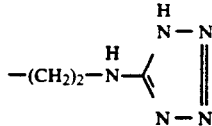 | 232-233 |
| 22 | $(H_3C)_3C-$ | H | $-(CH_2)_2-$ | $-N(C_2H_5)_2$ | 116-117 |
| 23 | $(H_3C)_3C-$ | H | $-(CH_2)_2-$ | $-O-(CH_2)_2-OC_2H_5$ | oil |

Pharmacological testing and results

The testing of the compounds of the formula I according to the invention for antiinflammatory action, influence on immunopathological processes, oxygen free radicaldeactivating properties and influence on arachidonic acid metabolism was carried out in the animal models and bioassays described in the following.

1. Adjuvant arthritis for influencing the antiinflammatory action (Table 2)

The investigations were carried out by the method of Pearson (Arthrit. Rheum. 1959, 2, 44). Male rats of a Wistar-Lewis strain having a body weight between 130 and 200 g were used as experimental animals. The compounds to be tested were administered orally (p. o.) once daily from the 1st to the 5th experimental day in doses of 50 mg per kg of body weight. The animals of one control group received only the vehicle. Each preparation group and the control group comprised 8 animals. The percentage reduction of the paw volume increase compared to that of the untreated control group was used as the criterion of action. The $ED_{50}$ values were determined graphically from the dose-response curve.

4-(3,5-Di-tert.-butyl-4-hydroxyphenyl)-2-methylthiazole i.e. the compound of the formula

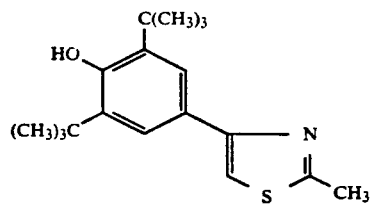

according to US-A-4,535,165 mentioned at the beginning, was additionally included in this and the investigation below as a comparison preparation.

TABLE 2

| | Antiinflammatory action on the 5th day | |
|---|---|---|
| Compound from example | Adjuvant arthritis (% inhibition at 50 mg/kg orally) | $ED_{50}$ value |
| 1 | 73 | 5.7 |
| 3 | 84 | 0.9 |
| 4 | 54 | |
| 5 | 51 | |
| 6 | 70 | |
| 7 | 83 | 2.4 |
| 10 | 71 | |
| 11 | 63 | 12.6 |
| 13 | 74 | |
| 14 | 61 | |
| 15 | 67 | 2.6 |
| 17 | 67 | 7.5 |

TABLE 2-continued

| | Antiinflammatory action on the 5th day | |
|---|---|---|
| Compound from example | Adjuvant arthritis (% inhibition at 50 mg/kg orally) | $ED_{50}$ value |
| 19 | 75 | 2.5 |
| 20 | 66 | |
| 21 | 65 | |
| Comparison preparation | 67 | |

2. Inhibition of immunopathological processes

It is generally recognized that the progressive course of inflammatory rheumatic diseases is principally caused by dysfunctions of the immune system and thus a more causal therapy can succeed only with those medicaments which inhibit these immunopathological processes.

a) Adjuvant arthritis (Perper modification)

The animals were only treated from the 1st to the 12th experimental day in the experimental arrangement described in item 1. After a treatment-free interval of 9 days, determination of the paw volume of the left and right hind paw was carried out on the 21st day (compare Table 3). In this test classical non-steroidal antiinflammatories are inactive as they are unable to inhibit the immunopathological processes underlying the chronic inflammatory phase. In addition, the results clearly prove the superiority of the compounds of the formula I according to the invention to the comparison preparation from US-A-4,535,165, which shows only a suggested action in the Perper modification of adjuvant arthritis.

TABLE 3

| Compound from example | Dose mg/kg/day | % inhibition on the 21st day | |
|---|---|---|---|
| | | Left paw | Right paw |
| 1 | 50 | 45 | 49 |
| 3 | 2.5 | 65 | 59 |
| | 5 | 41 | 74 |
| 5 | 50 | 20 | 42 |
| 11 | 50 | 44 | 51 |
| 13 | 50 | 44 | 31 |
| 14 | 50 | 22 | 49 |
| 15 | 50 | 39 | 50 |
| 17 | 50 | 60 | 38 |
| 19 | 5 | 59 | 70 |
| | 10 | 72 | 85 |
| 20 | 50 | 50 | 35 |
| 21 | 50 | 42 | 54 |
| Comparison preparation | 50 | 12 | 21 | b) Reverse passive Arthus reaction

Male Sprague-Dawley rats having a body weight between 100 and 120 g. which had been divided into groups of 8 animals in each case, were used as experimental animals. The animals received a subplantar injection in the left hind paw of 0.5 mg of immunoglobulin in 0.1 ml of a sodium chloride solution 1 hour after oral administration of the test substance. After 4 hours, the Arthus reaction was measured, the percentage change in the paw volume increase compared to that of the control group treated only with vehicle being used as a measuring parameter for the action.

According to Table 4, for example, the following compounds according to the invention are distinguished as potent inhibitors of the Arthus reaction:

TABLE 4

| Compound from example | Dose mg/kg orally | % inhibition |
| --- | --- | --- |
| 5 | 60 | 38 |
| 8 | 60 | 38 |
| 18 | 100 | 50 |
| 19 | 50 | 45 |
| 15 | 100 | 47 |
| 21 | 50 | 48 |

3. Action as free radical scavengers and as inhibitors of arachidonic acid metabolism a) Free radical scavenger properties The testing in this test, which allows conclusions on the antioxidative potential of a substance, was carried out according to Smith et al., Biochem, Pharmacol. 1987. 36, 1456. In this test, the reaction of the compounds according to the invention with the stable free radical 1,1-diphenyl-2-picrylhydrazyl (DPPH) is monitored optically at 20° C. The rate constant K and reaction orders n in Table 5 were determined graphically in the customary manner.

TABLE 5

| Compounds from example | k | n |
| --- | --- | --- |
| 1 | 2.24 | <1 |
| 2 | 0.39 | 1 |
| 3 | 0.70 | <1 |
| 7 | 0.44 | 1 |
| 8 | 0.30 | 1 |
| 9 | 0.46 | <1 |
| 11 | 0.16 | 1 |
| 12 | 0.51 | 1 |
| 13 | 0.07 | 1 |
| 15 | 3.50 | <1 |
| 16 | 1.22 | <1 |
| 18 | 0.42 | 1 |
| 19 | 6.60 | <1 |
| 21 | 0.43 | 1 | b) Arachidonic acid metabolism

The inhibitory action of the compounds according to the invention is measured on the in vitro arachidonic acid degradation catalyzed by cyclooxycenase and lipoxycenase with the aid of the test systems described in Weithmann and Alpermann, Arzneim.-Forsch. 1985, 35, 947: The cyclooxygenase-catalyzed synthesis of prostaglandins from arachidonic acid is measured in the microsomal cyclooxygenase system (fraction from sheep seminal vesicles, Paesel, Frankfurt, Germany). The coenzyme is adrenaline, whose conversion to adrenochrome is monitored by spectrophotometry at 492 nm. Cis-9-cis-12-linoleic acid is incubated with lipoxygenase (L7127, Sigma, Deisenhofen, Germany) in the lipoxygenase system in vitro and the formation of conjugated double bonds taking place during the oxygenation reaction is monitored optically at 234 nm.

The inhibitor actions, or the inhibitor concentrations necessary for a 50 % inhibition of enzyme activity ($IC_{50}$ values), have been determined for the following examples according to the invention:

Lipxoygenase (enzyme)
  Example 8: $IC_{50}=50$ μM
  Example 12: at 50 μM: 73 % inhibition
  Example 15: at 100 μM: 78 % inhibition
Cyclooxygenase (microsomes)
  Example 7: at 100 μM: 75 % inhibition
  Example 8: at 100 μM: 75% inhibition
  Example 16: $IC_{50} = 34$ μM Moreover, the substances according to the invention were also characterized in cellular leukocyte systems in vitro as inhibitors of arachidonic acid metabolites. To detect the lipoxygenase metabolites, human neutrophils stimlated by calcium ionophore A 23 187 (70 mcmol/l) were incubated with $^{14}C$-arachidonic acid (81 mcmol/l) and the principal metabolites formed after 15 minutes at 37° C., such as 5-hydroxyeicosatetraenoic acid (5-HETE) and the more strongly proinflammatory leukotriene $B_4$ ($LTB_4$) were determined quantitatively (Tab. 6) with the aid of a radio monitor after separation by HPLC. The influence on the proinflammatory arachiconic acid metabolites thromboxane and $LTB_4$ in cultures prepared from rat mast cells was determined in a corresponding manner (Tab. 7).

TABLE 6

Influence of the compounds according to Examples 7 and 9 on the activity of $LTB_4$ and 5-HETE formation in human neutrophils. (n = number of measurements).

| | $LTB_4$ formation | | | |
| --- | --- | --- | --- | --- |
| Example 7 Inhibitor Concentration n | 100 μM 9 | 10 μM 6 | 1 μM 6 | 0.1 μM 6 |
| Residual activity (%) | 1.7 ± 1.3 | 35 ± 17 | 74.3 ± 21.5 | 91.0 ± 13.2 |
| | 5-HETE formation | | | |
| Example 7 Inhibitor Concentration n | 100 μM 9 | 10 μM 6 | 1 μM 6 | 0.1 μM 6 |
| Residual activity (%) | 1.7 ± 0.4 | 39 ± 12.8 | 87.0 ± 15.6 | 89.2 ± 12.1 |
| | $LTB_4$ formation | | | |
| Example 9 Inhibitor Concentration n | 100 μM 9 | 10 μM 6 | 1 μM 6 | 0.1 μM 6 |
| Residual activity (%) | 20.5 ± 11 | 73 ± 12 | 79 ± 11 | 70 ± 12 |
| | 5-HETE formation | | | |
| Example 9 Inhibitor Concentration n | 100 μM 9 | 10 μM 6 | 1 μM 6 | 0.1 μM 6 |
| Residual activity (%) | 21 ± 8 | 75 ± 13 | 80 ± 8 | 91.5 ± 10 |

TABLE 7

Influence of various concentrations of the compound according to Example 3 on the formation of $TXB_2$ and $LTB_4$ in mast cell cultures (rat).

| Example 3 | $TXB_2$ | $LTB_4$ |
| --- | --- | --- |
| | Residual activity (%) | |
| 100 μM | 28 ± 10 | 78 ± 14 |
| 10 μM | 94 ± 17 | 102 ± 9 |

TABLE 7-continued

Influence of various concentrations of the compound according to Example 3 on the formation of TXB$_2$ and LTB$_4$ in mast cell cultures (rat).

| Example 3 | TXB$_2$ | LTB$_4$ |
|---|---|---|
| | Residual activity (%) | |
| 1 μM | 113 ± 49 | 94 ± 12 |

We claim:

1. A 2-substituted 4-(3-alkyl-5-tert.-butyl-4-hydroxyphenyl)thiazole of the formula I

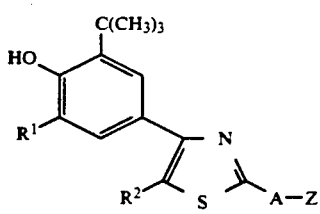

in which

R$^1$ is a saturated or unsaturated, straight-chain or branched C$_1$-C$_5$-alkyl group, R$^2$ is a hydrogen atom or an alkyl radical having 1 to 3 carbon atoms, A is an intermediate chain of the formula

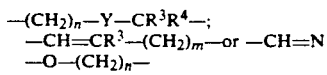

where

Y is a single bond, an oxygen or sulfur atom or a carbonyl group,

R$_3$ and R$_4$ are identical or different and are a hydrogen atom or an alkyl radical having up to two carbon atoms, m is a number from 0 to 3 and n is a number from 1 to 4, and Z is a tetrasole or CN group, or a radical of the formula

X is a hydroxyl group or a radical of the formula R$^5$O-or or R$^6$R$^7$N-, where R$^5$ is a straight-chain or branched C$_1$-C$_4$-alkyl radical which is optionally substituted by hydroxyl, C$_1$—C$_3$-alkoxy or C$_1$-C$_3$-alkylamino, R$_6$ and R$_7$ are identical or different and are a hydrogen atom, a straight-chain or branched C$_1$-C$_8$-alkyl radical or, for the case in which R$^6$ is a hydrogen atom or a C$_1$-C$_4$-alkyl radical, R$^7$ is a hydroxyl, a C$_1$-C$_3$-alkoxy or a tetrazol-5-yl group or X, together with the structural element —A—(C=O)—, is a radical of the formula II

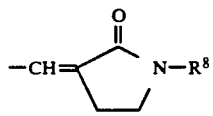

where R$_8$ is a hydrogen atom, a C$_1$-C$_3$ -alkyl radical or a C$_1$-C$_3$-alkoxy radical, or physiologically tolerable salts of such compounds of the formula I in which X is a hydroxyl or hydroxyamino group.

2. A compound as claimed in claim 1 of the formula I, in

R$^1$ is a tert.butyl or methyl group,

R$^2$ is hydrogen or methyl,

A is an intermediate chain of the formula

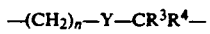

where Y is a single bond or an oxygen atom, R$^3$ and R$^4$ are identical or different and are a hydrogen atom or a methyl radical, and n is a number of 1 or 2, and X is a hydroxyl group or a radical of the formula R$^5$O-or R$^6$R$^7$N-, where R is a straight-chain or branched C$_1$-C$_3$-alkyl radical, R$_6$ is a hydrogen atom or a methyl radical and R$^7$ is a hydroxyl, methoxy or tetrazol-5-yl group.

3. A compound as claimed in claim 2 of the formula I, in which

R$^1$ is a tert.-butyl group

R$^2$ is hydrogen or methyl,

A is an intermediate chain of the formula

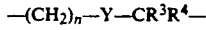

where Y is a single bond, R$^3$ and R$^4$ are a hydrogen atom and n is a number of 1 or 2 and X is a hydroxyl group or an R$^6$R$^7$N radical, where R$^6$ is a hydrogen atom or a methyl radical and R$^7$ is a hydroxyl or methoxy group.

4. A compound as claimed in claim 3, which is 3-(4-(3,5-di-tert.-butyl-4-hydroxyphenyl)thiazol-2-yl]propionic acid.

5. A pharmaceutical composition which comprises an effective amount of at least one of a compound of the formula I and claimed in claim 1 or said physiologically tolerable salts thereof together with a physiologically acceptable carrier.

6. The pharmaceutical composition as claimed in claim 5 for the prevention and treatment of diseases, in which the therapeutical administration of inhibitors of inflammation, immunomodulators, oxygen free radical-deactivating agents and/or inhibitors of arachidonic acid degradation mediated by 5-lipoxygenase and/or cyclooxygenase is indicated.

7. The pharmaceutical composition as claimed in claim 5, for the prevention and treatment of inflammatory diseases.

8. The pharmaceutical composition as claimed in claim 7 for the prevention and treatment of inflammatory rheumatic diseases.

* * * * *